(12) United States Patent
Elahi et al.

(10) Patent No.: US 8,977,367 B2
(45) Date of Patent: Mar. 10, 2015

(54) STIMULATION PROBE (71) Applicant: Sapiens Steering Brain Stimulation B.V., Eindhoven (NL)

(72) Inventors: Bijan Elahi, Eindhoven (NL); Sébastien Jody Ouchouche, Waalre (NL)

(73) Assignee: Sapiens Steering Brain Stimulation B.V., Eindhoven (NL)

( * ) Notice: Subject to any disclaimer, the term of this patent is extended or adjusted under 35 U.S.C. 154(b) by 0 days.

(21) Appl. No.: 14/104,212

(22) Filed: Dec. 12, 2013

(65) Prior Publication Data

US 2014/0172058 A1 Jun. 19, 2014

Related U.S. Application Data (60) Provisional application No. 61/736,924, filed on Dec. 13, 2012.

(30) Foreign Application Priority Data

Dec. 13, 2012 (EP) .................... 12196959

(51) Int. Cl.
| | | |
|---|---|---|
| A61N 1/00 | (2006.01) |
| A61N 1/05 | (2006.01) |
| A61B 5/04 | (2006.01) |
| A61B 5/0478 | (2006.01) |
| A61B 5/00 | (2006.01) |
| A61N 1/375 | (2006.01) |
| A61N 1/36 | (2006.01) |

(52) U.S. Cl.
CPC ............. *A61N 1/0534* (2013.01); *A61N 1/05* (2013.01); *A61B 5/04* (2013.01); *A61B 5/0478* (2013.01); *A61B 5/6868* (2013.01); *A61N 1/375* (2013.01); *A61B 5/04001* (2013.01); *A61B 5/4064* (2013.01); *A61B 5/4082* (2013.01); *A61N 1/0531* (2013.01); *A61N 1/36067* (2013.01); *A61N 1/36096* (2013.01); *A61B 2562/18* (2013.01)
USPC ........................................ 607/116

(58) Field of Classification Search
USPC .............................. 607/116, 48, 63
See application file for complete search history.

(56) References Cited

U.S. PATENT DOCUMENTS

| | | | |
|---|---|---|---|
| 5,632,643 A | 5/1997 | Shepherd et al. | |
| 6,151,520 A | 11/2000 | Combs | |
| 7,941,202 B2 | 5/2011 | Hetke et al. | |
| 2004/0064174 A1 | 4/2004 | Belden | |
| 2005/0070972 A1* | 3/2005 | Wahlstrand et al. | 607/48 |
| 2007/0050005 A1 | 3/2007 | Lauro | |
| 2010/0267265 A1 | 10/2010 | Dilmaghanian | |
| 2010/0318160 A1* | 12/2010 | Stevenson et al. | 607/63 |
| 2011/0232964 A1 | 9/2011 | Hashimoto et al. | |

FOREIGN PATENT DOCUMENTS

WO 2010/055453 A1 5/2010

OTHER PUBLICATIONS

International Search Report mailed Mar. 18, 2014 for International Patent Application No. PCT/EP2013/076370.

* cited by examiner

*Primary Examiner* — Robert N Wieland
(74) *Attorney, Agent, or Firm* — Shumaker & Sieffert, P.A.

(57) ABSTRACT

A stimulation probe comprises a lead having a distal end and a proximal end. The distal end of the lead has a plurality of electrodes configured to stimulate tissue. A protective tubing element extends over a portion of the lead proximate the proximal end of the lead. An advanced lead can element includes a switch matrix. The advanced lead can element is coupled to the proximal end of the lead and configured to couple the lead to an implantable pulse generator.

40 Claims, 6 Drawing Sheets

STIMULATION PROBE

CROSS-REFERENCE TO RELATED APPLICATIONS

This application claims the benefit of U.S. Provisional Patent Application No. 61/736,924 filed Dec. 13, 2012 entitled "A Probe, Especially A Probe For Neural Applications" and European Patent Application No. 12 196 959.6 filed Dec. 13, 2012 entitled "A Probe, Especially A Probe For Neural Applications", which are incorporated by reference herein in their entirety.

BACKGROUND OF THE INVENTION

The present invention generally relates to a stimulation probe. In some embodiments, the probe is configured for neural applications such as for neurostimulation and/or in neurorecording systems. The present invention also relates to neurostimulation and/or neurorecording systems, a protective tubing element and an advanced lead can element.

BRIEF SUMMARY OF THE INVENTION

In one embodiment there is a probe comprising: at least one lead; at least one protective tubing element at least partially arranged over and/or around the lead; and an advanced lead can element coupled to the at least one lead. In one embodiment, the at least one lead comprises a proximal end and a distal end, wherein the at least one protective tubing element is at least partially arranged over and/or around the proximal end of the at least one lead. In one embodiment, the protective tubing element is connected and/or connectable to the advanced lead can element by a fastening mechanism. In one embodiment, the fastening mechanism is configured such that the protective tubing element on the proximal end of the lead and the advanced lead can element are mechanically interlocked. In one embodiment, the fastening mechanism has a mechanical locking fit to lock in place the protective tubing element. In one embodiment, the protective tubing element is permanently attached or attachable to the advanced lead can element. In one embodiment, the fastening mechanism is configured such that the protective tubing element and/or the advanced lead can element comprises at least one part of the fastening mechanism.

In one embodiment, the protective tubing element comprises at least one reinforcement member. In one embodiment, the reinforcement member includes a helical spring or a braided mesh. In one embodiment, the protective tubing element comprises an outer layer. In one embodiment, the outer layer is at least partially comprised of a polymer. In one embodiment, the protective tubing element comprises an inner layer. In one embodiment, the inner layer is at least partially a lubricious substrate layer. In one embodiment, the lubricious substrate layer is comprised of HDPE, PTFE and/or PEEK. In one embodiment, the protective tubing element comprises a distal end having a lower hardness than the hardness of at least a part of the protective tubing element. In one embodiment, the distal end of the protective tubing has a durometer of less than approximately 20 Shore A. In one embodiment, the protective tubing element comprises a proximal end having the same or a higher hardness than the hardness of at least a part of the protective tubing element. In one embodiment, the proximal end of the protective tubing element comprises at least a part of the fastening mechanism so as to interlock the protective tubing element with the proximal end of the lead or the advanced lead can element.

In one embodiment, the protective tubing element comprises a length varying member configured to vary a length of the protective tubing element. In one embodiment, the length varying member includes two or more telescopic reinforced tubes of progressively smaller diameters which are nested within each other. In one embodiment, the advanced lead can element includes a switch matrix for deep brain stimulation electronics.

In another embodiment there is a neurostimulation and/or neurorecording system, comprising at least one a probe comprising: at least one lead; at least one protective tubing element at least partially arranged over and/or around the lead; and an advanced lead can element coupled to the at least one lead.

In another embodiment there is a stimulation probe comprising a lead having a distal end and a proximal end, the distal end of the lead having a plurality of electrodes configured to stimulate tissue; a protective tubing element extending over a portion of the lead proximate the proximal end of the lead; and an advanced lead can element including a switch matrix, the advanced lead can element coupled to the proximal end of the lead, the advanced lead can element configured to couple the lead to an implantable pulse generator.

In another embodiment there is a protective tubing element for a probe having a lead coupled to an advanced lead can element, the protective tubing element comprising: a proximal end and a distal end, the proximal end at least partially arranged over and/or around a proximal end of the lead. In one embodiment, the proximal end of the protective tubing element is connected and/or connectable to the advanced lead can element by a fastening mechanism. In one embodiment, the fastening mechanism has a mechanical locking fit to lock in place the protective tubing element. In one embodiment, the protective tubing element is permanently attached or attachable to the advanced lead can element. In one embodiment the protective tubing element further comprises at least one reinforcement member. In one embodiment, the reinforcement member includes a helical spring or a braided mesh. In one embodiment the protective tubing element further comprises an outer layer. In one embodiment, the outer layer is at least partially comprised of a polymer.

In one embodiment the protective tubing element further comprises an inner layer. In one embodiment, the inner layer is at least partially a lubricious substrate layer. In one embodiment, the lubricious substrate layer is comprised of HDPE, PTFE and/or PEEK. In one embodiment, the distal end has a lower hardness than the hardness of at least another part of the protective tubing element. In one embodiment, the distal end has a durometer of less than approximately 20 Shore A. In one embodiment the proximal end has the same or a higher hardness than the hardness of at least another part of the protective tubing element. In one embodiment, the proximal end of the protective tubing element comprises at least a part of the fastening mechanism so as to interlock the protective tubing element with a proximal end of the lead or the advanced lead can element. In one embodiment the protective tubing element further comprises a length varying member configured to vary a length of the protective tubing element. In one embodiment, the length varying member includes two or more telescopic reinforced tubes of progressively smaller diameters which are nested within each other.

In another embodiment there is an advanced lead can element for a probe having a lead comprising: a fastening mechanism configured to fasten to a protective tubing element at least partially arranged over and/or around the lead. In one embodiment, the fastening mechanism has a mechanical locking fit to lock in place the protective tubing element. In one embodiment the advanced lead can element further comprises a switch matrix for deep brain stimulation electronics.

BRIEF DESCRIPTION OF THE SEVERAL VIEWS OF THE DRAWINGS

The foregoing summary, as well as the following detailed description of embodiments of the stimulation probe, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These systems consist of a lead made from a thin film based on thin film technology, as e.g. described in WO 2010/055453 A1, which is hereby incorporated by reference in its entirety. The thin film leads are fixed on a stylet material to form a probe. These probes will have multiple electrode areas and will enhance the precision to address the appropriate target in the brain and relax the specification of positioning. Meanwhile, undesired side effects due to undesired stimulation of neighbouring areas may be minimized.

Leads that are based on thin film manufacturing are e.g. described by U.S. Pat. No. 7,941,202, which is hereby incorporated by reference in its entirety, and have been used in research products in animal studies.

In existing systems, probes (e.g., 1.27 mm in diameter and 10-50 cm long) are connected to an implantable pulse generator (IPG) using a connector (e.g., 3.8 mm in diameter and having 4 screw-contacts), by means of connector cables (e.g., 2.8 mm diameter and 110 mm long). The distal end of the probe has four concentric contacts that fit into the 4-contacts connector and the body of the probe is cylindrical until its end. As a consequence, the probe can pass easily through a microdrive assembly that guides the flexible probe and its stiff guiding wire into the brain tissue to the target.

Future systems will need more, smaller electrodes, in order to better control the delivery of electrical stimulation, because current stimulation causes mild to severe side-effects in about 30% of the patients. A larger number of electrodes mean a larger number of contacts to the connector, which in turn calls for different connector technologies, because it cannot be expected from the neurosurgeon to tighten ten or more individual screws for the ten or more contacts. Also, the contact sizes need to be smaller, certainly in the case of cranial implants.

The thin film of such a lead is fragile and can be damaged under crushing (from mechanical shocks on the head or clamping forces from the burr-plug) or sharp bending angles. Although one way to provide protection of the thin film is to increase the diameter of the lead, this option may not be feasible due to increased track length and hence increased track resistance, and further incompatibility with microdrive guides.

It is desired to keep the lead diameter small-commensurate with existing leads in the market (e.g., 1.27 mm outer diameter), while simultaneously provide protection of the thin film.

It is therefore an object of the present invention, to improve a probe, further a neurostimulation and/or neurorecording system, a protective tubing element and an advanced lead can element, particularly in that the overall reliability and safety of the whole system may be increased and that damages of the frangible thin film of the lead of the probe may be avoided and to create protection of the lead where protection is needed without substantially increasing the diameter or length of the lead in the distal section of the lead.

A probe may be provided comprising at least one lead and an advanced lead can element, wherein the probe comprises at least one protective tubing element, wherein the protective tubing element is at least partially arranged over and/or around at least a portion of the lead.

The probe can be a probe for neural applications, for example, or, more specifically for brain applications, preferably for a neurostimulation and/or neurorecording system. Such a neurostimulation and/or neurorecording system may be e.g. a DBS system.

By this, the overall reliability and safety of the whole system is increased and damages of the frangible thin film of the lead of the probe may be avoided. Furthermore, protection of the lead may be assured where protection is needed without substantially increasing the diameter or length of the lead in the distal section of the lead.

The lead may comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or merely the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

The advanced lead can element may comprise electronics to address the plurality of electrodes and at least one advanced lead can connecting member. Further, the advanced lead can element may be hermetically or merely hermetically sealed and may comprise electronics to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are merely evenly distributed arranged all over the distal end of the lead.

Additionally, it is possible that the lead comprises a proximal end and a distal end, wherein the protective tubing element is at least partially arranged over and/or around the proximal end of the lead. The proximal end of the lead is the section of the lead which is connected or connectable to the advanced lead can element and includes the electrodes 132. Consequently, in this section of the lead protection of the lead and the thin film is preferred and of advantage, since the proximal end of the lead may be subject to bending or the like and crushing forces.

Furthermore it is possible that the protective tubing element is connected and/or connectable to the advanced lead can element by a fastening mechanism so as to interlock with the proximal end of the lead or the advanced lead can element. In particular, the protective tubing element may be connected and/or connectable to the advanced lead can element by fastening mechanism so as to mechanically interlock with the proximal end of the lead or the advanced lead can element.

Moreover it is possible that the fastening mechanism is configured such that the protective tubing element the proximal end of the lead or the advanced lead can element may be mechanically interlocked.

The fastening mechanism may have a snap-fit design or a bayonet locking system or hooks or grips or any other mechanical structures that may be used to lock in place the protective tubing element. The fastening mechanism may be configured such that the protective tubing element is permanently attached or attachable to the advanced lead can element. The fastening mechanism may be configured such that the protective tubing element and/or the advanced lead can element comprises at least one part of the fastening mechanism and/or that at least two parts of the fastening mechanism are counterparts.

Furthermore, it is possible that the protective tubing element comprises at least one reinforcement member. In one embodiment, the reinforcement member comprises or is a helical spring or a braided mesh. The reinforcement member may be comprised of metal (e.g., 304V stainless steel, titanium or the like) or at least partially made of hard polymers such as PEEK.

Additionally, it is possible that the protective tubing element comprises an outer layer, wherein the outer layer is at least partially made of polymer, wherein exemplarily the polymer is silicone or polyurethane or the like. For instance, such an outer layer of the protective tubing element may be made at least partially of at least one polymer such as silicone on polyurethane for varying the durability of the outer layer. With the appropriate choice of material and surface treatment (for instance microblasting), the outer surface of the tubing may be made slightly sticky/tacky. By this, the advantage is achieved that a good retention force is provided when the protective tubing is pinched by the burr hole cap.

Moreover it is possible that the protective tubing element comprises an inner layer, wherein the inner layer is at least partially embodied as a lubricious substrate layer, wherein exemplarily the lubricious substrate layer is a HDPE layer and/or a PTFE layer or a PEEK liner. For instance, the advantage is achieved that a lubricious substrate layer of HDPE or PTFE offers reduced surface friction so that any contact between the lead and the protective tubing element would not damage the lead or make the insertion of the protective tubing over the lead difficult or impossible.

It is further possible that the protective tubing element comprises a distal end having a lower hardness or durometer than the hardness of at least a part of the protective tubing element, wherein exemplarily the distal end is embodied as a soft distal end at least partially made of a low hardness (durometer) polyurethane and/or that the distal end is attached to the protective tubing element by thermobonding or the like. For instance, the distal end may be embodied as a so-called soft distal end. The soft distal end may be made of low durometer polyurethane and attached to the reinforced part of the tubing via thermo bonding. The soft distal end may smooth the transition between the protective tubing element and the lead and may also act as a seal or closing lips preventing fluid ingress beneath the protective tubing.

Moreover, it is possible that the protective tubing element comprises a proximal end having the same or a higher hardness (durometer) than the hardness (durometer) of at least a part of the protective tubing element and/or that the proximal end is attached to the protective tubing element by thermo-bonding or the like. For instance a so-called hard proximal end made of higher durometer polyurethane may be used and attached to the reinforced part of the protective tubing element via thermo bonding.

Furthermore it is possible that the proximal end comprises at least a part of the fastening mechanism so as to interlock with the proximal end of the lead or the advanced lead can element. For instance, the proximal end may feature a fastening mechanism to mechanically interlock the protective tubing element with the proximal end of the lead or the advanced lead can.

Moreover, it is possible that the protective tubing element comprises a length varying means and is configured such that the length of the protective tubing element can be varied.

Additionally, it is possible that the length varying means comprises two or more telescopic reinforced tubes of progressively smaller diameters which are nested within each other.

Figure 1:
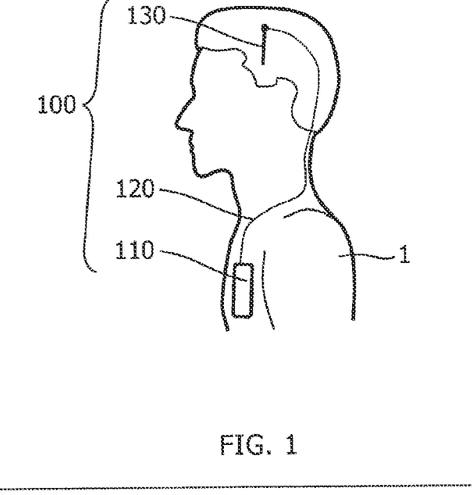
FIG. 1 is a schematic drawing of a neurostimulation system for deep brain stimulation (DBS) in accordance with an exemplary embodiment of the present invention.

Further details and advantages of the present invention shall be described hereinafter with respect to the drawings:

An embodiment of a neurostimulation system 100 for deep brain stimulation (DBS) is shown in FIG. 1. The neurostimulation system 100 may comprise at least a controller 110 that may be surgically implanted in the chest region of a patient 1, typically below the clavicle or in the abdominal region of patient 1. The controller 110 may be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

Figure 2:
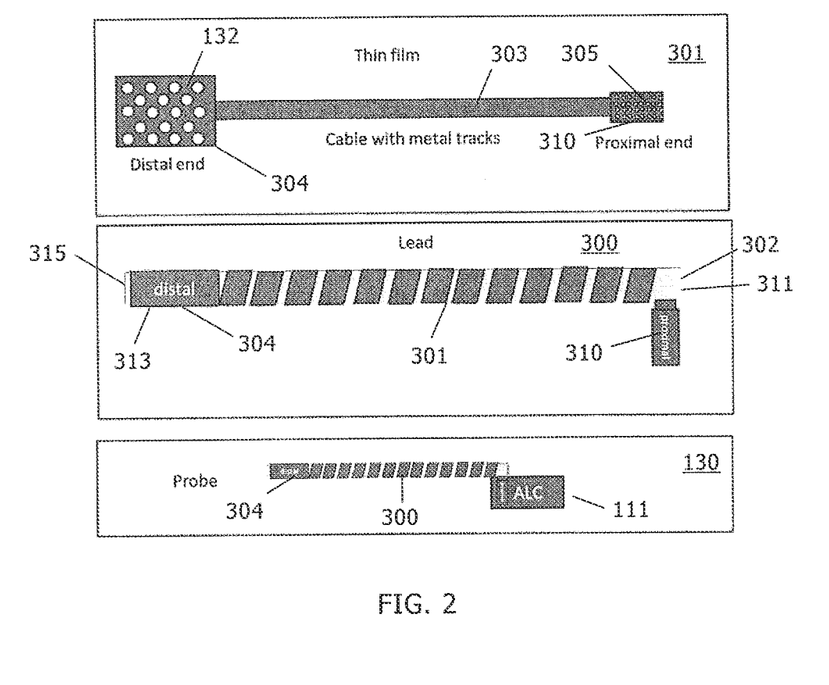
FIG. 2 is a schematic drawing of a probe neurostimulation system for deep brain stimulation (DBS) and its components.

FIG. 2 further illustrates a typical architecture for a Deep Brain Stimulation probe 130 that comprises a DBS lead 300 and an advanced lead can element 111 comprising electronics to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the advanced lead can element 111. The advanced lead element 111 may comprise the switch matrix of the DBS steering electronics. The distal end 304 of the lead 300 may comprise the electrodes 132 for the brain stimulation. The proximal end 310 of the lead 300 comprises the interconnect contacts 305 for each metal line in the cable 303. The cable 303 comprises metal lines (not shown) to connect each distal electrodes 132 to a designated proximal contact 305.

Figure 3:
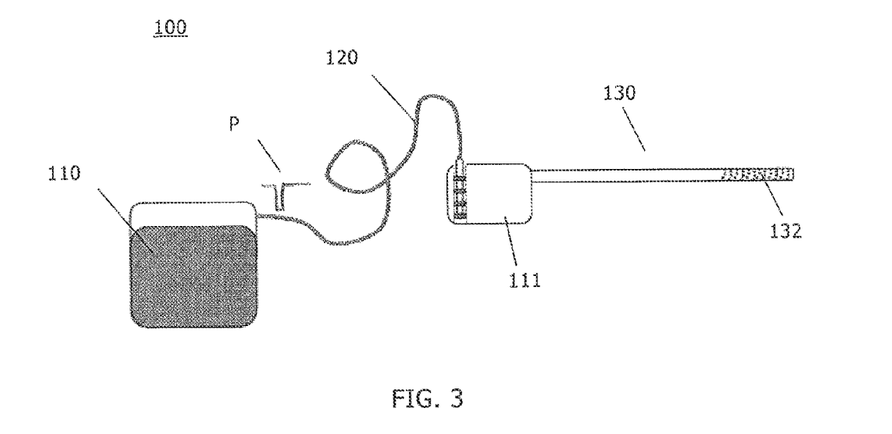
FIG. 3 is a schematic drawing of a probe system in accordance with an exemplary embodiment of the present invention.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby electrodes 132 (e.g. 64 electrodes 132) are provided on outer body surface at the distal end of the probe 130. By means of the extension wire 120 pulses P supplied by controller 110 may be transmitted to the advanced lead can 111. The controller 110 may be an implantable pulse generator (IPG) 110.

Figure 4:
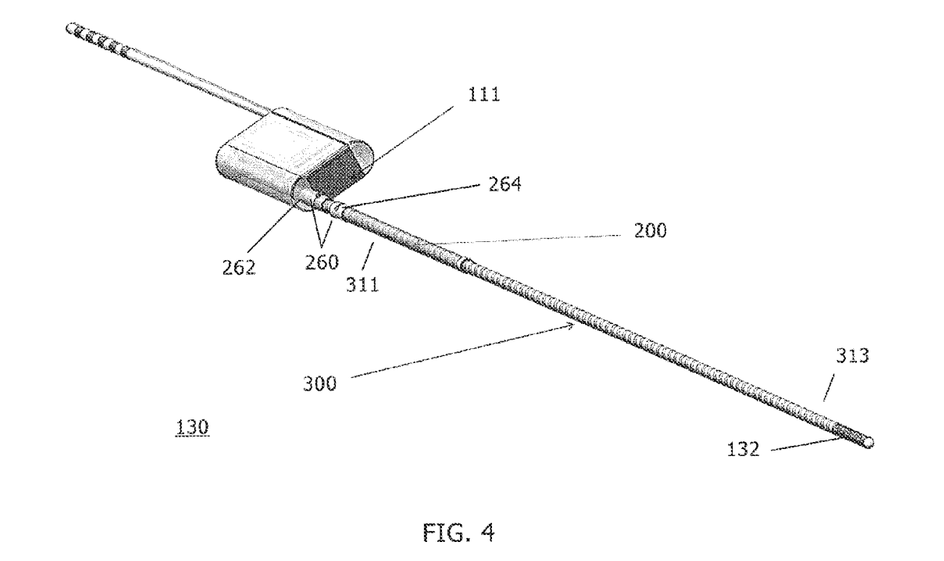
FIG. 4 is a perspective view of a probe system in accordance with an exemplary embodiment of the present invention.

FIG. 4 shows a further schematic drawing of the probe system according to the present invention, which is slightly different when compared with the embodiment shown in FIG. 3. In particular, FIGS. 3 and 4 show different concepts of connectivity. However, the main and essential features of the invention realised in both embodiments shown in FIGS. 3 and 4.

The probe 130 is according to embodiment shown in FIG. 4 a probe 130 for neural applications, here a probe 130 for a neurostimulation and/or neurorecording system. The neurostimulation and/or neurorecording system is a deep brain stimulation system 100 as shown in FIGS. 1 and 2.

The probe 130 comprises a lead 300 and an advanced lead can element 111 and also a protective tubing element 200.

The protective tubing element 200 is partially arranged over and around the lead 300. As can be seen in FIG. 4, the lead 300 comprises a proximal end 311 and a distal end 313. The protective tubing element 200 is arranged over and around the proximal end 311 of the lead 300.

Figure 5:
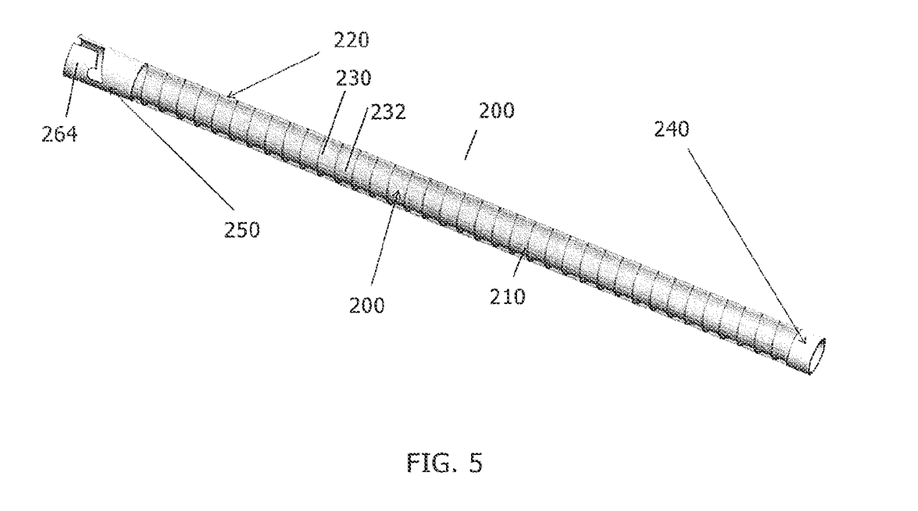
FIG. 5 is a perspective view of a protective tubing element used in a probe system in accordance with an exemplary embodiment of the present invention.

As further shown in FIGS. 4 and 5, the protective tubing element 200 is connectable to the advanced lead can element 111 by a fastening mechanism 260 so as to interlock the protective tubing element 200 with the advanced lead can element 111. Alternatively, the proximal end 311 of the lead 300 may be connected or connectable to the protective tubing element 200.

The fastening mechanism 260 is configured such that the protective tubing element 200 and the advanced lead can element 111 comprise each one part 262, 264 of the fastening mechanism 260. The at least two parts 262, 264 of the fastening mechanism 260 are counterparts. So, the proximal end 250 (see FIG. 5) comprises a first part 264 of the fastening mechanism 260 so as to interlock with the advanced lead can element 111 comprising the second part 262 of the fastening mechanism 260. The proximal end 250 is a so-called hard proximal end made of higher durometer polyurethane and attached to the reinforced part, i.e. reinforcement member 210 of the protective tubing 200 element via thermo bonding.

Alternatively and not shown, the second part of the fastening mechanism 260 may be at the proximal end 311 of the lead 300 so as to interlock the first part 264 of the fastening mechanism 260 of the protective tubing element 200 with the second part of the fastening mechanism 260 at the proximal end 311 of the lead 300.

The protective tubing element 200 comprises a reinforcement member 210 (see FIG. 5), wherein the reinforcement member 210 comprises or is a helical spring 210 or a braided mesh. This helical spring 210 may preferably embodied as an at least partially metallic reinforcement helical spring 210 (for instance 304V stainless steel, titanium or the like) or at least partially made of hard polymers such as PEEK.

Furthermore, the protective tubing element 200 comprises an outer layer 220, wherein the outer layer 220 is at least partially made of polymer, wherein the polymer may be silicone or polyurethane or the like. For instance, such an outer layer 220 of the protective tubing element 200 may be made at least partially of of at least one polymer such as silicone on polyurethane for varying the durometer of the outer layer. With the appropriate choice of material and surface treatment (for instance microblasting), the outer surface of the protective tubing element 200 may be made slightly sticky/tacky. By this, the advantage is achieved that a good retention force is provided when the protective tubing is pinched by the burr hole cap.

Moreover, the protective tubing element 200 comprises an inner layer 230, wherein the inner layer 230 is at least partially embodied as a lubricious substrate layer 232, wherein exemplarily the lubricious substrate layer 232 could be an HDPE layer or a PTFE layer or a PEEK layer. For instance, the advantage is achieved that such an inner layer 230, i.e. a lubricious substrate layer of HDPE or PTFE offers reduced surface friction so that any contact between the lead 300 and the protective tubing element 200 may not damage the lead 300 or make the insertion of the protective tubing over the lead difficult or impossible.

The protective tubing element 200 comprises a distal end 240 having a lower hardness than the hardness of at least a part of the protective tubing element 200, wherein exemplarily the distal end 240 is embodied as a soft distal end 240 at least partially made of a low durometer polyurethane. In one embodiment, the distal end 240 has a durometer of approximately 15 Shore A to approximately 70 Shore D. In one embodiment, the distal end 240 has a durometer of approximately 20 Shore A. In one embodiment, the distal end 240 has a durometer of less than approximately 20 Shore A. Further, the distal end 240 may be attached to the protective tubing element 200 by thermobonding or the like.

Here, the distal end 240 is embodied as a so-called soft distal end 240. The soft distal end 240 may be made of low durometer polyurethane and attached to the reinforced part, i.e. the reinforcement member 210 of the protective tubing element 200 via thermo bonding. The soft distal end 240 smoothes the transition between the protective tubing element 200 and the lead 300 and may also act as a seal or closing lips preventing fluid ingress beneath the protective tubing element 200.

According to the embodiment of FIGS. 4 and 5, the fastening mechanism 260 is configured such that the protective tubing element 200 and the advanced lead can element 111 may be mechanically interlocked. Here, the fastening mechanism 260 may have a bayonet locking system.

It is also possible that the proximal end 311 of the lead 300 and the protective tubing element 200 may be mechanically interlocked. For example, as further interlocking alternatives a snap-fit design or hooks or grips or any other mechanical structures that may be used to lock in place the protective tubing element 200 relative to the advanced lead can 111 or the lead 300 may be used.

Figure 6:
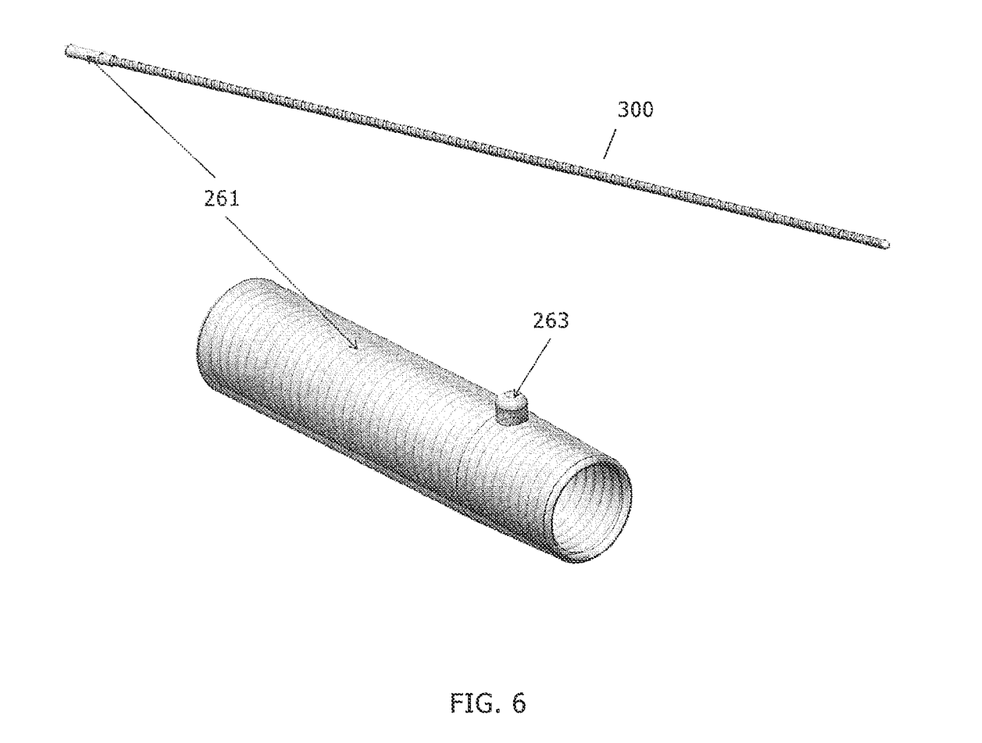
FIG. 6 is a perspective and partially enlarged view of the proximal part of the connector for protective tubing element shown in FIG. 5.

In the case of a bayonet mount design, the hard proximal end 250 could consist of a tapered short tubing with a slot 265 selectively laser removed that matches a radial pin 263 placed on the proximal sleeve 261 of the lead 300 as shown in FIG. 6. As can be seen in FIG. 4, the proximal sleeve 261 may be mounted and fixated into the advanced lead can element 111.

Figure 7:
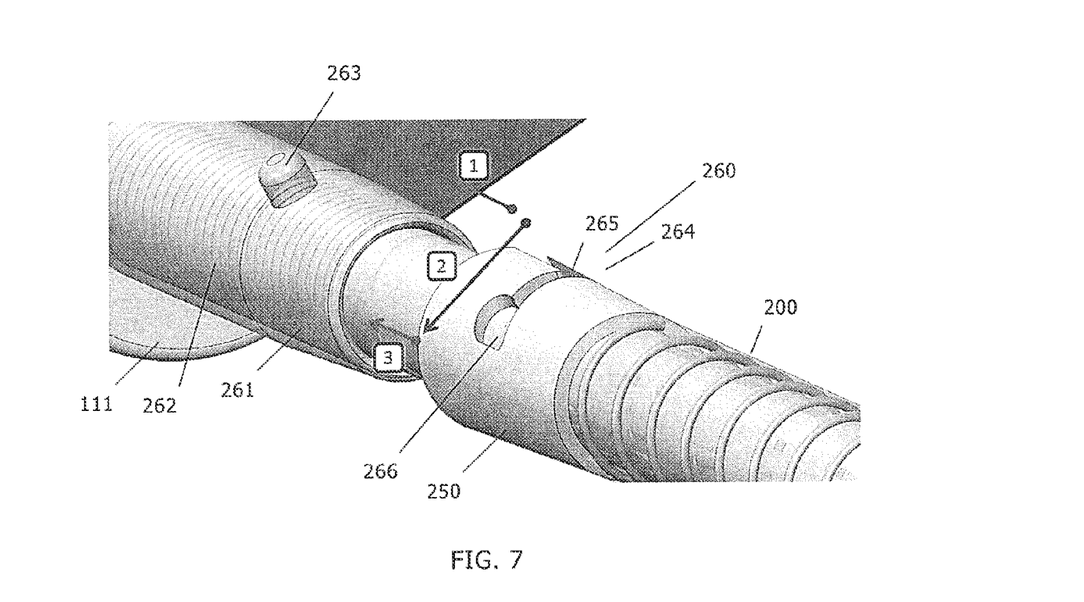
FIG. 7 is an enlarged perspective view of a fastening mechanism of the probe shown in FIG. 5.

To couple the protective tubing element 200 to the lead 300/advanced lead can 111, the slot 265 of the hard proximal end 250 is aligned with the pin 263 of the lead sleeve 261 and the protective tubing 200 is gently pushed toward the advanced lead can 111 (Step 1 as shown in FIG. 7). Once the pin 263 reached the bottom of the slot 265, the protective tubing element 200 is rotated so that the pin 263 slides along the horizontal arm of the slot 265 until it reaches the "serif" 266 (Step 2 as shown in FIG. 7). The protective tubing element 200 is then slightly pulled back to have the pin 263 locked into the "serif" 266 (Step 3 as shown in FIG. 7).

To disconnect, the protective tubing element 200 is pushed toward the advanced lead can 111 to move the pin 263 out of the "serif" 266 while twisting it in the opposite direction than for connecting, and then pulled apart. With proper design of the slot 265 width, this fastening mechanism 260 would provide an audible "click" to provide positive feedback to the surgeon, when the interlock has occurred or disengaged.

The active lead package will contain several protective tubing elements of different length that the surgeon would pick from, in order to accommodate different depths of insertion.

The inner diameter of the protective tubing element 200 may be for example approximately 1.3 mm, wide enough to slip over the lead 300. The outer diameter of the protective tubing element may be approximately 1.7 mm so it may slide through common application devices for DBS lead's like a Ben's Gun. In one embodiment, the protective tubing element 200 is slidingly coupled to the lead 300. In other embodiments, the protective tubing element 200 is rigidly secured (e.g., press fit, adhesive and/or mechanical attachment) to the outer surface of the lead 300.

Figure 8:
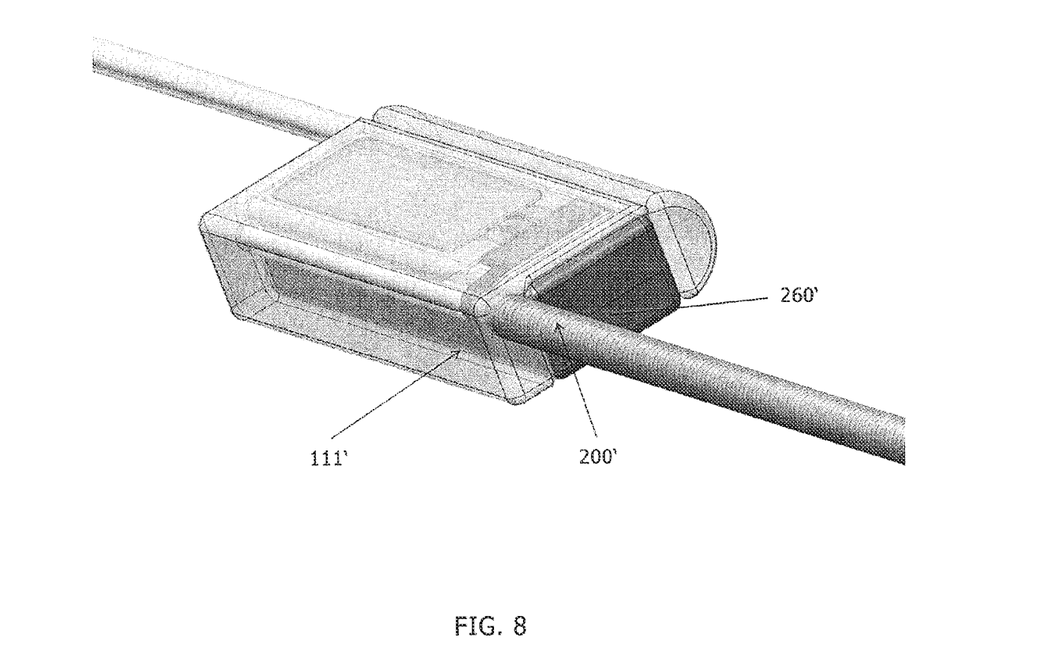
FIG. 8 is a perspective view of an advanced lead can and protective tubing element in accordance with an exemplary embodiment of the present invention.

FIG. 8 shows a perspective view of the advanced lead can element 111' and the protective tubing element 200' in a further embodiment of the present invention. As shown in FIG. 8, the fastening mechanism 260' may be configured such that the protective tubing element 200' is permanently attached or attachable to the advanced lead can element 111'. According to the embodiment shown in FIG. 8, the protective tubing element 200' may be encapsulated within the header of the advanced lead can element 111'.

The protective tubing element 200' may be permanently attached to the advanced lead can element 111', for instance by means of adhesives applied between the protective tubing element 200' and the body of the lead 300 (not shown in FIG. 8) or between the protective tubing element and the advanced lead can element 111'. Potential adhesives and encapsulant include silicone adhesive, UV-curable adhesive, epoxy, urethanes etc.

The protective tubing element 200' and the advanced lead can element 111' may be embodied (except the connection) likewise the protective tubing element 200 and the advanced lead can element 111.

Figure 9:
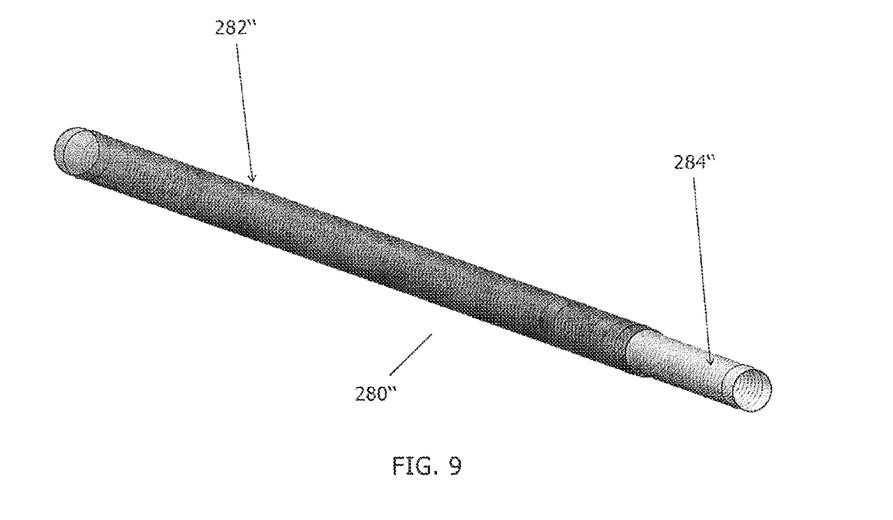
FIG. 9 is a perspective view of a protective tubing element in accordance with an exemplary embodiment of the present invention.
Figure 10:
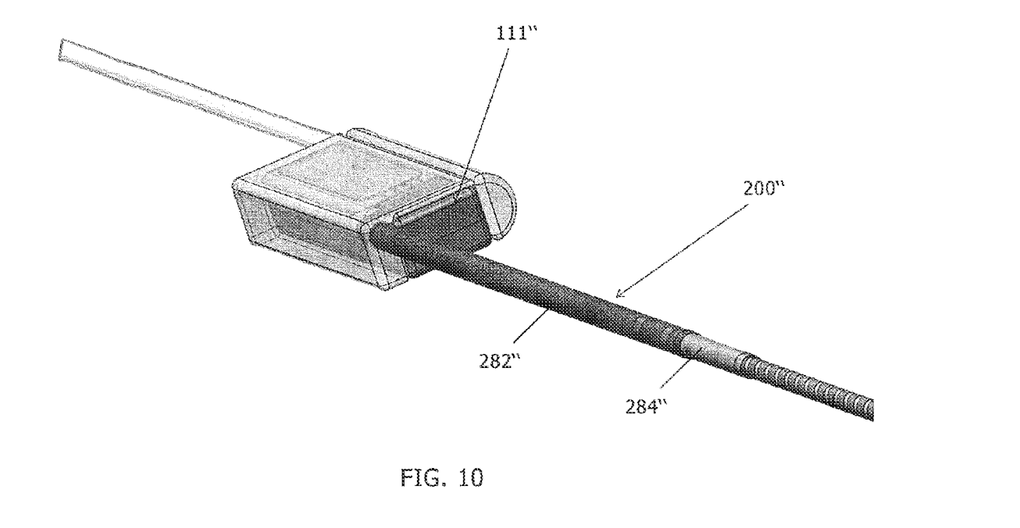
FIG. 10 is a perspective view of the advanced lead can and the protective tubing element shown in FIG. 9.
Figure 11A:
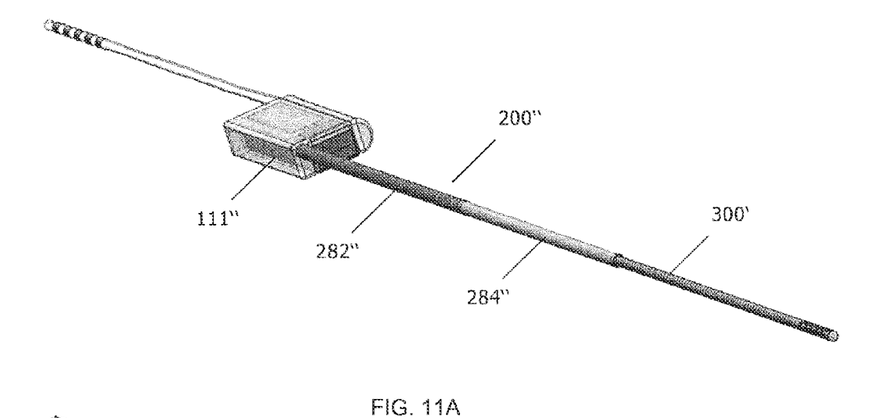
FIG. 11A is a perspective view of the advanced lead can and the protective tubing element according to the embodiment shown in FIGS. 9 and 10 in a partially extended state.
Figure 11B:
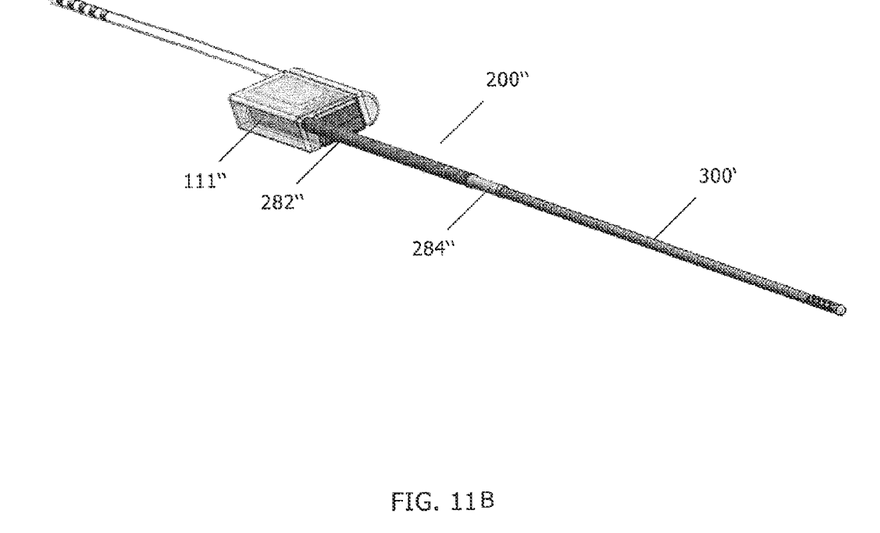
FIG. 11B is a perspective view of the advanced lead can and the protective tubing element according to the embodiment shown in FIGS. 9 and 10 in a partially refracted state.

According to the embodiment shown in FIGS. 9 to 11 the protective tubing element 200" attached to the advanced lead can 111" comprises a length-varying member 280" and is configured such that the length of the protective tubing element 200" may be varied over the length of the lead 300.

The length varying member 280" according to the embodiment shown in FIG. 9 comprises two or more telescopic reinforced tubes 282", 284" of progressively smaller diameters are nested within each other. So, an example of a 2-stage telescopic protective tubing element 200" may be provided which is capable of providing a long protection of the lead body from a very compact refracted length.

FIG. 11A shows the protective tubing element 200" is partially extended state, i.e. tube 284" is partially pulled out of tube 282" and both tubes 282" and 284" are covering lead 300 over a larger length when compared with the partially retracted state and in FIG. 11B in the partially retracted state, tube 284" is merely refracted into tube 282" both tubes 282" and 284" are covering lead 300 over a smaller length when compared with the partially extended state.

All other features of the protective tubing element 200" may be embodied likewise the embodiments of the protective tubing elements 200, 200' as shown in FIGS. 4 to 8 and described above.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:
1. A probe comprising:
at least one lead;
at least one protective tubing element at least partially arranged over and/or around the at least one lead; and
an advanced lead can element coupled to the at least one lead,
wherein the at least one lead comprises a proximal end and a distal end, and
wherein the at least one protective tubing element is at least partially arranged over and/or around the proximal end of the at least one lead.

2. The probe according to claim 1, wherein the at least one protective tubing element is connected and/or connectable to the advanced lead can element by a fastening mechanism.

3. The probe according to claim 2, wherein the fastening mechanism is configured such that the at least one protective tubing element and the advanced lead can element are mechanically interlocked.

4. The probe according to claim 2, wherein the fastening mechanism has a mechanical locking fit to lock in place the at least one protective tubing element.

5. The probe according to claim 2, wherein the at least one protective tubing element is permanently attached or attachable to the advanced lead can element.

6. The probe according to claim 2, wherein the fastening mechanism is configured such that the at least one protective tubing element and/or the advanced lead can element comprises at least one part of the fastening mechanism.

7. The probe according to claim 1, wherein the at least one protective tubing element comprises at least one reinforcement member.

8. The probe according to claim 7, wherein the reinforcement member includes a helical spring or a braided mesh.

9. The probe according to claim 1, wherein the at least one protective tubing element comprises an outer layer.

10. The probe according to claim 9, wherein the outer layer is at least partially comprised of a polymer.

11. The probe according to claim 1, wherein the at least one protective tubing element comprises an inner layer.

12. The probe according to claim 11, wherein the inner layer is at least partially a lubricious substrate layer.

13. The probe according to claim 12, wherein the lubricious substrate layer is comprised of HDPE, PTFE and/or PEEK.

14. A probe comprising:
at least one lead;
at least one protective tubing element at least partially arranged over and/or around the at least one lead; and
an advanced lead can element coupled to the at least one lead, wherein the at least one protective tubing element comprises a distal end having a lower hardness than the hardness of at least another part of the at least one protective tubing element.

15. A probe comprising:
at least one lead;
at least one protective tubing element at least partially arranged over and/or around the at least one lead; and
an advanced lead can element coupled to the at least one lead,
wherein a distal end of the at least one protective tubing element has a durometer of less than approximately 20 Shore A.

16. A probe comprising:
at least one lead;
at least one protective tubing element at least partially arranged over and/or around the at least one lead; and
an advanced lead can element coupled to the at least one lead,
wherein the at least one protective tubing element comprises a proximal end having the same or a higher hardness than the hardness of at least another part of the at least one protective tubing element.

17. The probe according to claim 16, wherein the proximal end of the at least one protective tubing element comprises at least a part of a fastening mechanism so as to interlock the at least one protective tubing element with a proximal end of the at least one lead or the advanced lead can element.

18. A probe comprising:
at least one lead;
at least one protective tubing element at least partially arranged over and/or around the at least one lead; and
an advanced lead can element coupled to the at least one lead,
wherein the at least one protective tubing element comprises a length varying member configured to vary a length of the at least one protective tubing element.

19. The probe according to claim 18, wherein the length varying member includes two or more telescopic reinforced tubes of progressively smaller diameters which are nested within each other.

20. The probe according to claim 1, wherein the advanced lead can element includes a switch matrix for deep brain stimulation electronics.

21. A neurostimulation and/or neurorecording system, comprising at least one probe according to claim 1.

22. A protective tubing element for a probe having a lead coupled to an advanced lead can element, the protective tubing element comprising:
a proximal end and a distal end, the proximal end at least partially arranged over and/or around a proximal end of the lead,
wherein the proximal end of the protective tubing element is connected and/or connectable to the advanced lead can element by a fastening mechanism.

23. The protective tubing element according to claim 22, wherein the fastening mechanism has a mechanical locking fit to lock in place the protective tubing element.

24. A protective tubing element for a probe having a lead coupled to an advanced lead can element, the protective tubing element comprising:
a proximal end and a distal end, the proximal end at least partially arranged over and/or around a proximal end of the lead, wherein the protective tubing element is permanently attached or attachable to the advanced lead can element.

25. A protective tubing element for a probe having a lead coupled to an advanced lead can element, the protective tubing element comprising:
a proximal end and a distal end, the proximal end at least partially arranged over and/or around a proximal end of the lead; and
at least one reinforcement member.

26. The protective tubing element according to claim 25, wherein the reinforcement member includes a helical spring or a braided mesh.

27. A protective tubing element for a probe having a lead coupled to an advanced lead can element, the protective tubing element comprising:

a proximal end and a distal end, the proximal end at least partially arranged over and/or around a proximal end of the lead; and an outer layer.

28. The protective tubing element according to claim 27, wherein the outer layer is at least partially comprised of a polymer.

29. A protective tubing element for a probe having a lead coupled to an advanced lead can element, the protective tubing element comprising:

a proximal end and a distal end, the proximal end at least partially arranged over and/or around a proximal end of the lead; and an inner layer.

30. The protective tubing element according to claim 29, wherein the inner layer is at least partially a lubricious substrate layer.

31. The protective tubing element according to claim 30, wherein the lubricious substrate layer is comprised of HDPE, PTFE and/or PEEK.

32. A protective tubing element for a probe having a lead coupled to an advanced lead can element, the protective tubing element comprising:

a proximal end and a distal end, the proximal end at least partially arranged over and/or around a proximal end of the lead, wherein the distal end has a lower hardness than the hardness of at least another part of the protective tubing element.

33. A protective tubing element for a probe having a lead coupled to an advanced lead can element, the protective tubing element comprising:

a proximal end and a distal end, the proximal end at least partially arranged over and/or around a proximal end of the lead, wherein the distal end has a durometer of less than approximately 20 Shore A.

34. A protective tubing element for a probe having a lead coupled to an advanced lead can element, the protective tubing element comprising:

a proximal end and a distal end, the proximal end at least partially arranged over and/or around a proximal end of the lead, wherein the proximal end has the same or a higher hardness than the hardness of at least another part of the protective tubing element.

35. The protective tubing element according to claim 34, wherein the proximal end of the protective tubing element comprises at least a part of a fastening mechanism so as to interlock the protective tubing element with the proximal end of the lead or the advanced lead can element.

36. A protective tubing element for a probe having a lead coupled to an advanced lead can element, the protective tubing element comprising:

a proximal end and a distal end, the proximal end at least partially arranged over and/or around a proximal end of the lead; and further comprising a length varying member configured to vary a length of the protective tubing element.

37. The protective tubing element according to claim 36, wherein the length varying member includes two or more telescopic reinforced tubes of progressively smaller diameters which are nested within each other.

38. An advanced lead can element for a probe having a lead comprising:

a fastening mechanism configured to fasten to a protective tubing element at least partially arranged over and/or around the lead.

39. The advanced lead can element according to claim 38, wherein the fastening mechanism has a mechanical locking fit to lock in place the protective tubing element.

40. The advanced lead can element according to claim 38 further comprising:

a switch matrix for deep brain stimulation electronics.

* * * * *